United States Patent [19]

Theeuwes

[11] Patent Number: 4,915,689
[45] Date of Patent: Apr. 10, 1990

[54] PARENTERAL DELIVERY SYSTEM COMPRISING A VIAL CONTAINING A BENEFICIAL AGENT

[75] Inventor: Felix Theeuwes, Los Altos, Calif.

[73] Assignee: ALZA Corporation, Palo Alto, Calif.

[21] Appl. No.: 832,194

[22] Filed: Feb. 24, 1986

Related U.S. Application Data

[63] Continuation of Ser. No. 620,371, Jun. 13, 1984, abandoned.

[51] Int. Cl.⁴ ............................................. A61M 37/00
[52] U.S. Cl. .......................................... 604/83; 137/3;
   137/9; 137/571; 604/51; 604/52; 604/82;
   604/84; 604/93
[58] Field of Search ...................... 604/51, 52, 93, 82,
   604/83, 84; 137/571, 3, 9

[56] References Cited

U.S. PATENT DOCUMENTS 3,230,954  1/1966  Burgess et al. ................... 604/52

FOREIGN PATENT DOCUMENTS

0005606  11/1979  European Pat. Off. ............ 604/83

Primary Examiner—Asok Pal
Attorney, Agent, or Firm—Paul L. Sabatine; Edward L. Mandell; Steven F. Stone

[57] ABSTRACT

A parenteral delivery system for delivering a beneficial agent is disclosed. The delivery system comprises a reservoir containing a medical fluid, a vial containing a beneficial solid agent, and a manifold for establishing fluid communication between the reservoir and the vial.

16 Claims, 7 Drawing Sheets

0
PARENTERAL DELIVERY SYSTEM COMPRISING A VIAL CONTAINING A BENEFICIAL AGENT

CROSS REFERENCE TO RELATED APPLICATION

This application is a continuation of U.S. patent application Ser. No. 06/620,371 filed June 13, 1984, now abandoned.

FIELD OF THE INVENTION

This invention pertains to a delivery system that can be used for delivering a beneficial agent parenterally including intravenously. The delivery system comprises a reservoir of a parenterally administrable fluid, a vial of a beneficial parenterally administrable agent, and means for conveying fluid, from the reservoir into the vial for forming a parenterally administrable solution.

BACKGROUND OF THE INVENTION

The parenteral administration, including intravenous administration of a beneficial agent is commonly used in clinical practice. Presently, the beneficial agent is administered using a parenteral delivery system that contains a premixed formulation comprising a parenterally administrable fluid and the agent. The premixed formulation is administered from a container suspended above a patient. While this form of parenteral administration is widely used and often leads to successful therapy, there is still a great deal of dissatisfaction with this type of parenteral delivery system. For example, with the parenteral systems now in use, the agent is premixed with the fluid and this frequently requires storing the parenteral system at a lower temperature to prevent degradation of the beneficial agent. Also, beneficial agents that are fluid sensitive and require formulation with the solution at the time of administration, cannot be administered with these prior art systems.

DETAILED DESCRIPTION OF THE DRAWINGS

Figure 1:
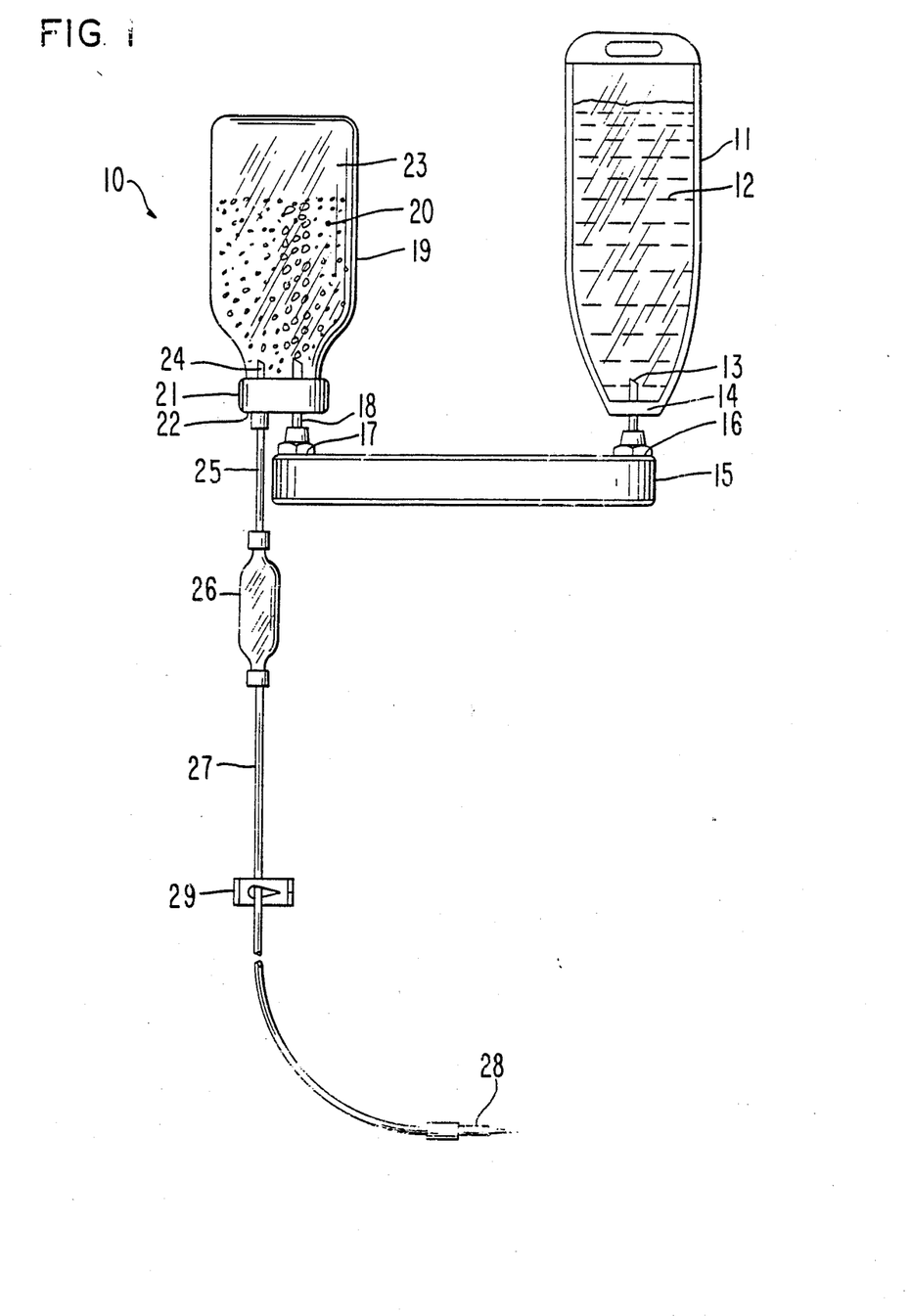
FIG. 1 is a perspective view of a parenteral delivery system provided by the invention comprising a manifold for establishing fluid contact between a fluid reservoir and a vial of beneficial agent.

FIG. 1 represents a parenteral delivery system 10 provided by the invention. Parenteral delivery system 10 comprises a reservoir 11 of a medical fluid 12 acceptable for parenteral including intravenous administration. Reservoir 11 in the embodiment illustrated in FIG. 1 is made of plastic, preferably flexible, transparent nontoxic plastic. In the embodiment illustrated, reservoir 11 is shaped like a bag formed from a non-toxic polyolefin, polyvinyl chloride, or the like. In another embodiment reservoir 11 can be made of glass having the shape of a conventional glass container. Reservoir 11 is connected to the rest of delivery system 10 through spike 13, which spike 13 pierces bottom 14 of reservoir bag 11. Spike 13 is hollow and it is optionally integrally formed or suitably connected to means 15. Means 15 is used for conveying fluid 12 from reservoir 11 to the rest of delivery system 10. In one presently preferred embodiment, means 15 is a manifold structure with inlet position 16 for receiving spike 13 and outlet position 17 for supporting outgoing spike 18. The lateral inlet and outlet spikes are a means for functionally engaging the manifold, and they are also a means for letting fluid 12 into manifold 15 and a means for letting fluid 12 exit manifold 15.

Spike 18 is hollow having a bore that extends therethrough and it conveys fluid 12 from manifold 15 into a vial 19. Vial 19 is shown in vertical position; however it should be understood that the manifold 15 can be journaled to hold vial 19 in horizontal, vertical upright, or inverted position, or in any useful position in 360° around axis A and B. Spike 18 enters the mouth area 22 of vial 19, which vial is designed to contain a beneficial, parenterally including an intravenously administrable agent 20. Vial 19 is a small closed container preferably made from glass, or in another embodiment vial 19 is made from a rigid, clear transparent plastic. Vial 19 is suitably capped by closure rim 21 that surrounds and engages the external surface of vial 19 and the region of vial 19 that defines and forms mouth 22 of vial 19. Closure rim 21 holds a stopper in the mouth of vial 19, not seen in FIG. 1. Spike 18 pierces the stopper for establishing fluid communication between manifold 15 and the internal lumen 23 of vial 19. Vial 19 initially does not contain any fluid, however vial 19 has a capacity of about 5 cc to 350 cc, more or less, and it can store about 10 nanograms to 425 grams, more or less of a beneficial agent.

Medical fluid 12 enters vial 19 through spike 18 and it forms an administrable medical solution with agent 20 in vial 19. The medical solution containing agent 20 leaves vial 19 through spike 24. Spike 24 has its fluid inlet end inside vial 19, and its other end, or fluid outlet end is outside vial 19. Spike 24 is hollow and it extends through mouth 22 of vial 19. The other end of spike 24 is connected to a section of medical grade tubing 25. Tubing 25 is suitably connected to a drip chamber 26. Drip chamber 26 is preferably transparent and it is made from glass or clear plastic. Drip chamber 26 is used to trap air and is used, in cooperation with a regulator clamp 29, for adjusting the rate of flow of medical fluid containing the beneficial agent from vial 19 as the flow proceeds dropwise through delivery system 10. Drip chamber 26 is connected through a second section of medical tubing 27 to skin piercing delivery member 28. Tube 27 passes through regulator clamp 29 used for regulating the rate of fluid flow through system 10.

Medical fluid 12 is typically a sterile solution, such as a solution of dextrose, a solution of an electrolyte, or saline. Medical fluid 12 also is a pharmaceutical vehicle, or a pharmaceutically acceptable carrier for beneficial agent 20 that is to be administered to a recipient. The initial volume of medical fluid 12 in container 11 will be a volume sufficient for performing a preselected therapeutic program. Container 11 can be a small volume container, or container 11 can be a large volume container. Container 11 as presently used herein, generally will have for the former container a capacity of about 100 cc to 350 cc, and the latter container will have a capacity of 250 cc to 1000 cc. Containers of other capacities likewise can be used for the present purpose.

The beneficial agent 20 in vial 19 can be in any pharmaceutical state that forms an agent formulation solution with medical fluid 12 that enters vial 19. The use of vial 19 with agent 20 therein does not require any reconstituting, or admixture prior to use. The term beneficial agent as used here includes drugs, which drugs are administrable to a recipient. The latter term embraces warm-blooded animals which expressly includes humans. The pharmaceutically acceptable form that can be used in vial 19 is in a presently preferred embodiment solid. For the purpose of this invention, the term solid includes crystalline, microcrystalline, particle, pellet, granule, powder, tablet, dry, spray-dried, lyophilize, compressed powder, compressed granule, friable layers, forms that disintegrate and dissolve in the presence of incoming medical fluid, and the like. Vial 19 generally contains an amount of beneficial agent for executing a prescribed therapeutic program, that is, an amount of agent for the preprogrammed delivery of a therapeutically effective amount of agent to the recipient to produce a beneficial therapeutic effect.

Figure 2:
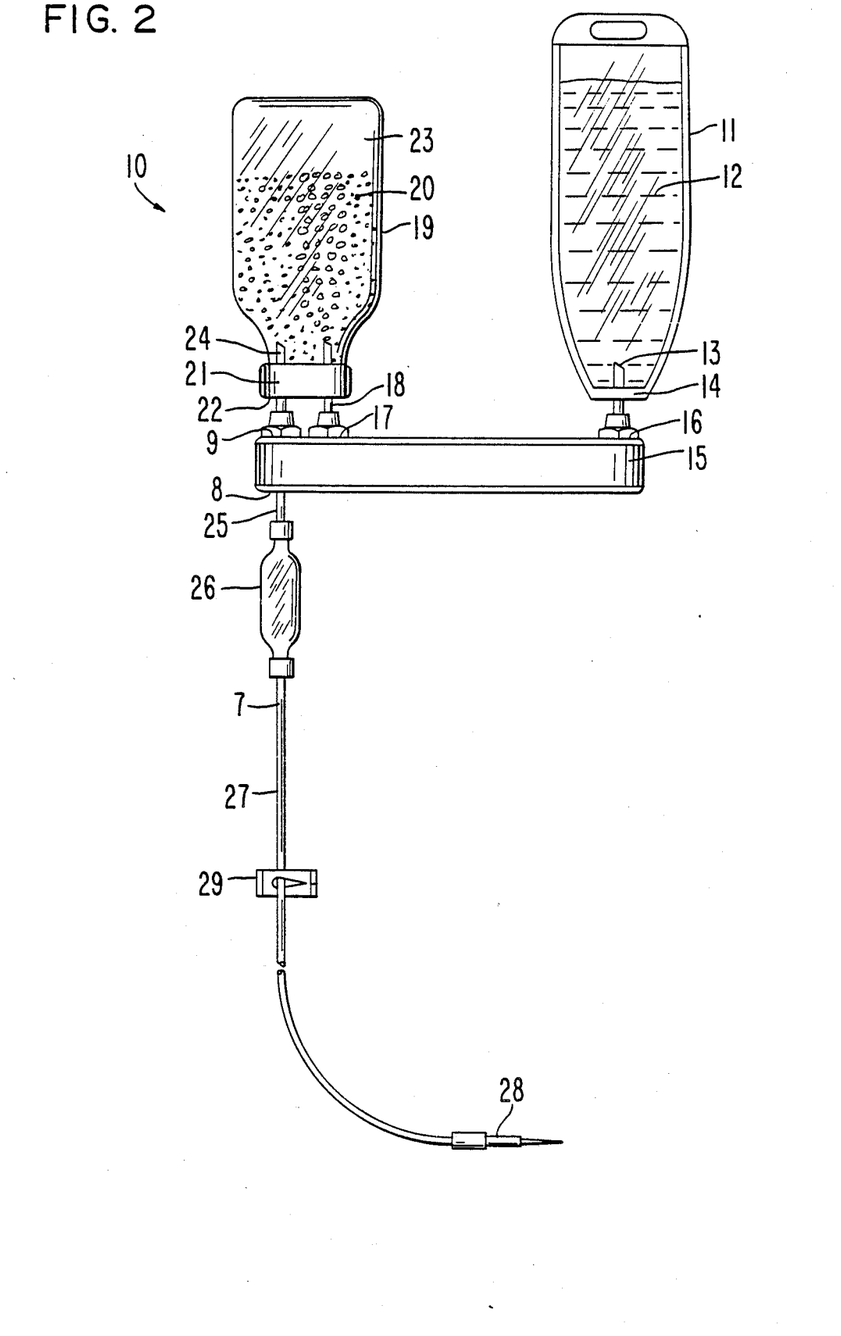
FIG. 2 is a perspective view of a delivery system similar to the delivery system of FIG. 1 depicting the vial and a primary line suitably connected to the manifold.

FIG. 2, taken in conjunction with FIG. 1 depicts delivery system 10 using another embodiment of manifold 15 as provided by the invention. In FIG. 2, manifold 15 is provided with an inlet area 9 for receiving spike 24 coming from vial 19. Manifold 15 also is provided with an outlet area 8 for suitably connecting primary fluid path 7 to manifold 15. The embodiment of manifold 15 depicted in FIG. 2 provides a means for conveying a medical solution from vial 19 directly into primary path 7 for administration to a needy recipient.

Figure 3:
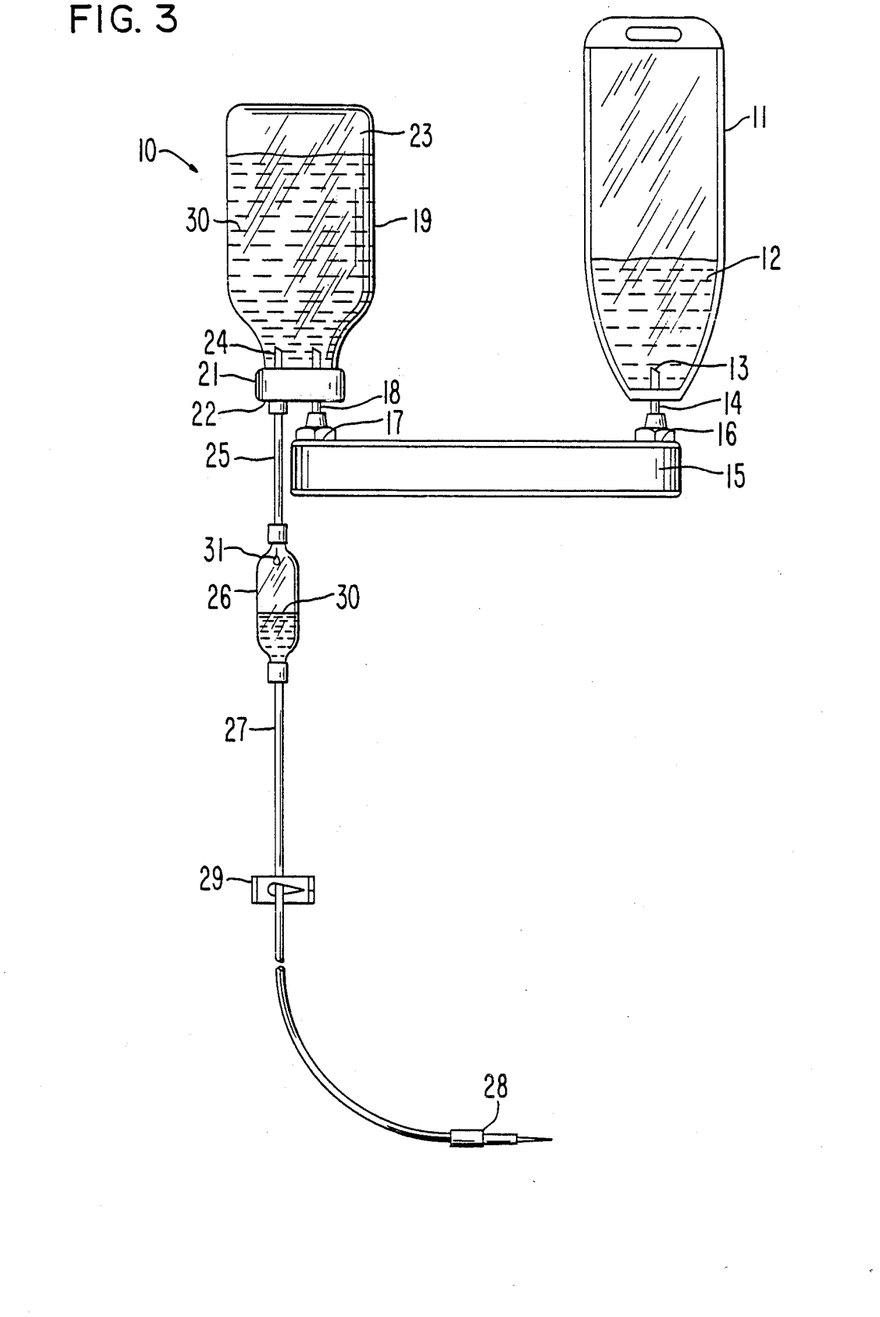
FIG. 3 illustrated the delivery system in one embodiment in operation formulating an administrable solution in situ.

FIG. 3, taken in conjunction with FIGS. 1 and 2 depicts parenteral delivery system 10 in operation formulation a parenterally administrable solution 30 that contains the beneficial agent. Delivery system 10 operates by fluid initially flowing from a full container 11 through spike 14 into manifold 15. The fluid 12 height in reservoir 11 is preferably higher than its height in vial 19, and in a presently preferred embodiment the level of base 14 should not be lower than the level of base 22. In another embodiment, an elevated position can be achieved for reservoir 11 by elevating reservoir 11 and connecting a tube to spike 13 and manifold 15, not shown, thereby establishing fluid communication between reservoir 11 and manifold 15. Fluid 12, in operation in all instance, continues its flow through manifold 15 through spike 18 and hence into vial 19. Incoming medical fluid 12 forms in situ an administrable solution 30 with agent 20 in vial 19. Medical solution 30 leaves vial 19 through spike 24. Spike 24 conveys medical solution 30 containing agent 20 dropwise 31 into drip chamber 26, at a rate of flow regulated by downstream regulatory clamp 29. Medical solution 30 continues its flow through tube 27 to skin-piercing means 28 for administration to a recipient. Further in operation, as the level of medical fluid 12 drops in container 11 it correspondingly increases in vial 19. Also, as medical solution 30 is administered to a recipient over a period of time, the level of medical solution 30 in vial 19 correspondingly drops to an insignificant level over a corresponding period of time.

Figure 4:
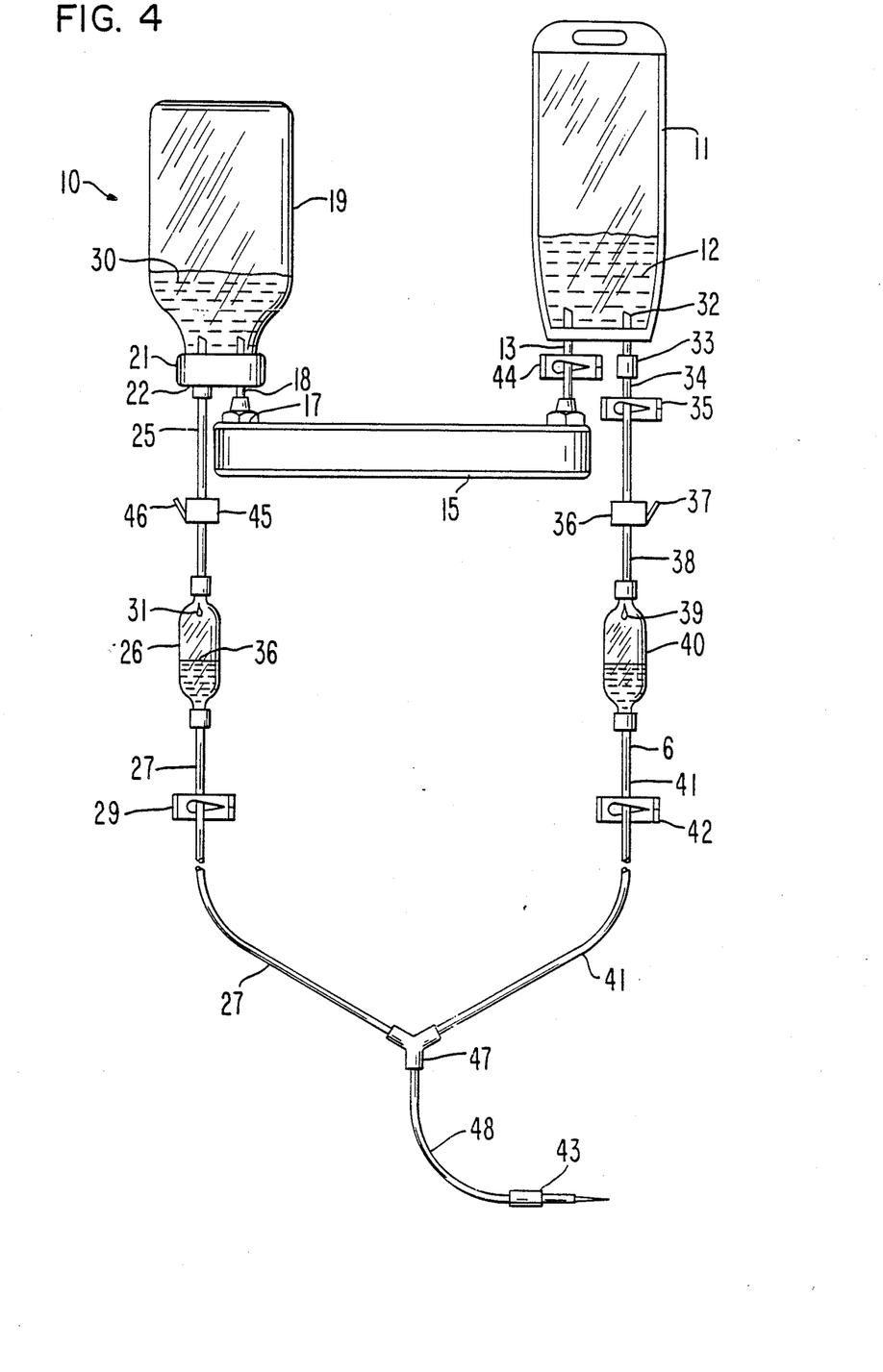
FIG. 4 illustrates another delivery system provided by the invention comprising a primary fluid flow path, a secondary fluid flow path, and a manifold for conveying fluid.

FIG. 4 depicts another embodiment provided by the invention. FIG. 4 is similar to FIGS. 1, 2 and 3; however, FIG. 4 contains a secondary fluid path 6 that lets medical fluid 12 by-pass the primary fluid path comprising vial 19. The secondary fluid path 6 is a means for administering medical fluid 12 free of added beneficial agent 20 directly to a patient. The secondary fluid path 6 or bypass line comprises a hollow spike 32 that enters container 11 and connects to coupling member 33. A section of medical tubing 34 connected to coupling member 33 passes through regulator clamp 35 and conveys fluid 12 to an optional in-line filter 36. Filter 36 is equipped with an air vent 37 for letting air escape from the delivery system. Filter 36 is a means for removing bacterial and particulate matter such as traces of glass and plastic from the system. A section of medical tube 38 conveys fluid 12 flow dropwise 39 into drip chamber 40. A selection of tube 41 that passes through a flow regulator 42 conveys fluid 12 to Y-couple 47. Couple 47 is a means for joining fluid flow from the primary fluid path 7 and the secondary path 6 into a common flow path 48. Tube 48 is connected to a skin-piercing means 43 for administering fluid 12, or medical solution 30 to an animal. The delivery system illustrated in FIG. 4 additionally is equipped with a regulatory clamp 44 for preventing fluid 12 from entering manifold 15, or clamp 44 is used for adjusting the rate of flow of fluid 12 into manifold 15. The primary path of delivery system 10 that provides in situ formulation of medical solution 30 is optionally equipped in FIGS. 1, 2 and 3, and as seen in FIG. 4, with a filter 45 that has an air vent 46. Filter 45 removes undissolved agent, bacterial material and the like from the primary path. The delivery system illustrated in FIG. 4 provides for (1) the administration of medical fluid., (2) the administration of medical fluid containing beneficial agent; and (3) the simultaneous administration of medical fluid and medical fluid containing beneficial agent, thereby regulating the concentration of the agent in the fluid by adjusting the fluid flow rates.

Figure 5:
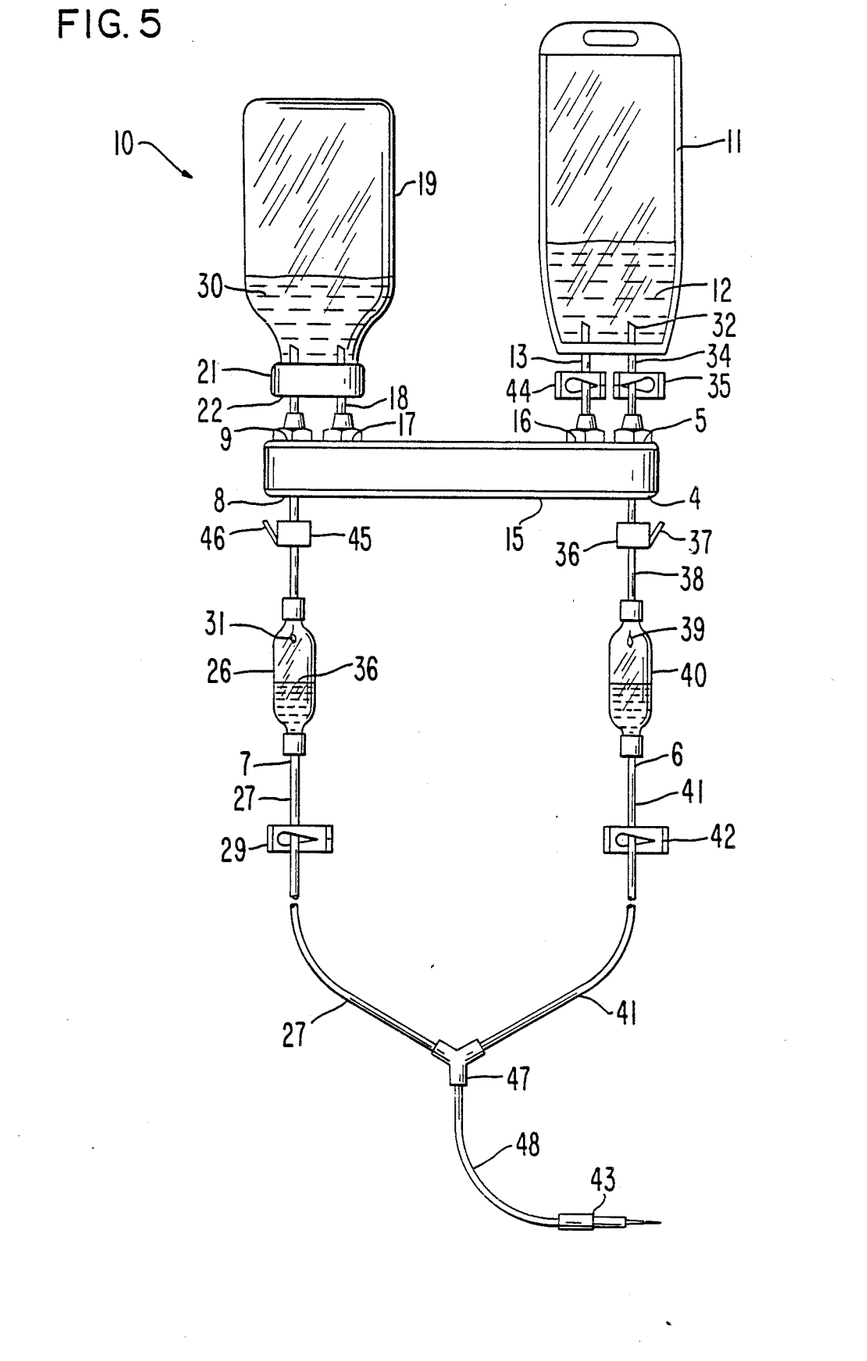
FIG. 5 illustrates a delivery system similar to the delivery system illustrated in FIG. 4 with the added embodiment consisting essentially of the reservoir, the vial, the primary path and the secondary path connected to the manifold.

FIG. 5, taken in conjunction with FIG. 4 depicts yet another embodiment provided by the invention. In FIG. 5, manifold 15 is designed and manufactured for receiving and supporting both vial 19 and reservoir 11 and both primary fluid path 7 and secondary fluid path 6. In FIG. 5, manifold 15 is provided with an inlet area 9 for receiving spike 24 coming from vial 19 and with an outlet area 8 for connecting primary path 7 to manifold 15. In FIG. 5, manifold 15 also is provided with an inlet area 5 for receiving incoming spike 32 and with an outlet area 4 for receiving secondary path 6. The embodiments depicted in FIG. 5 provide for conveying a medical solution 30 from vial 19 directly into primary path 7 and also for conveying medical fluid 12 from reservoir 11 directly into secondary path 6, for administration in both embodiments to a patient.

Figure 6:
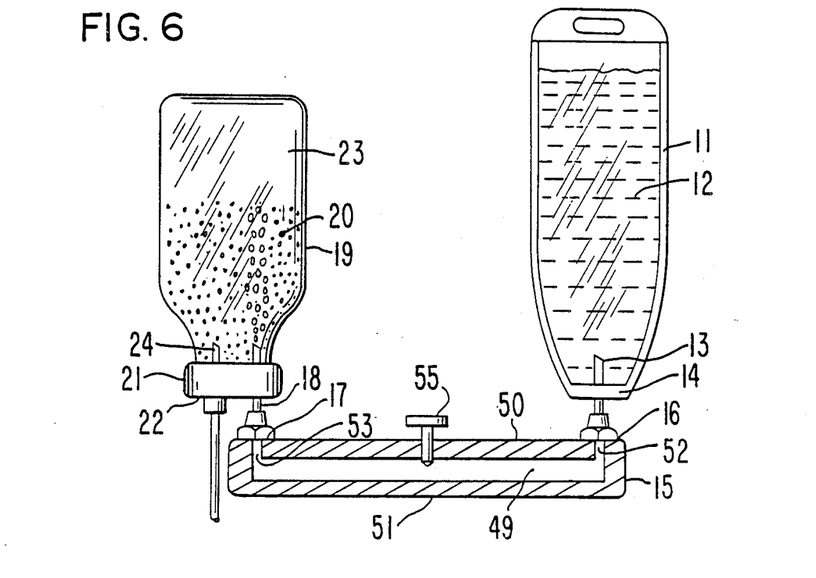
FIG. 6 illustrates a cross-section through one manifold provided by the invention.
Figure 7:
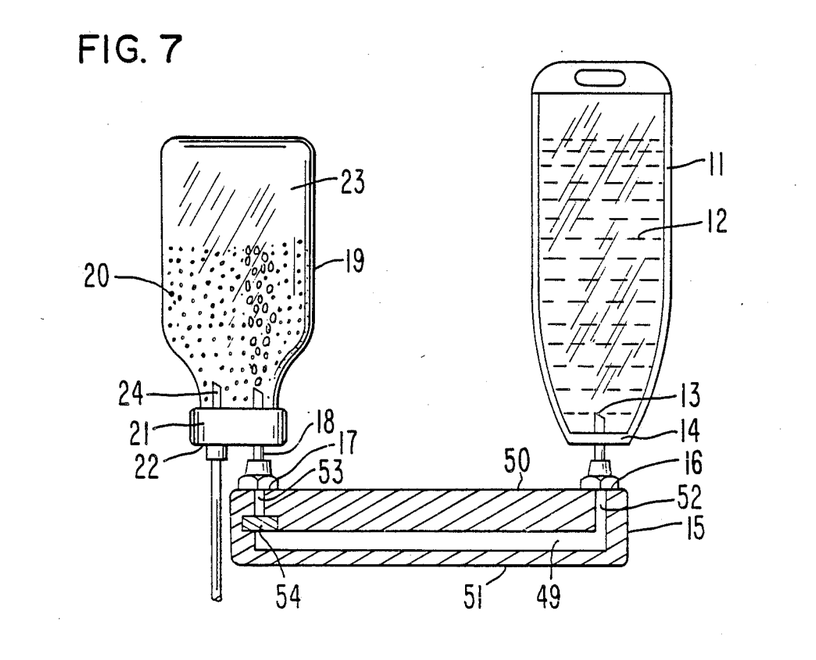
FIG. 7 illustrates a cross-section through a manifold housing a filter.
Figure 8:
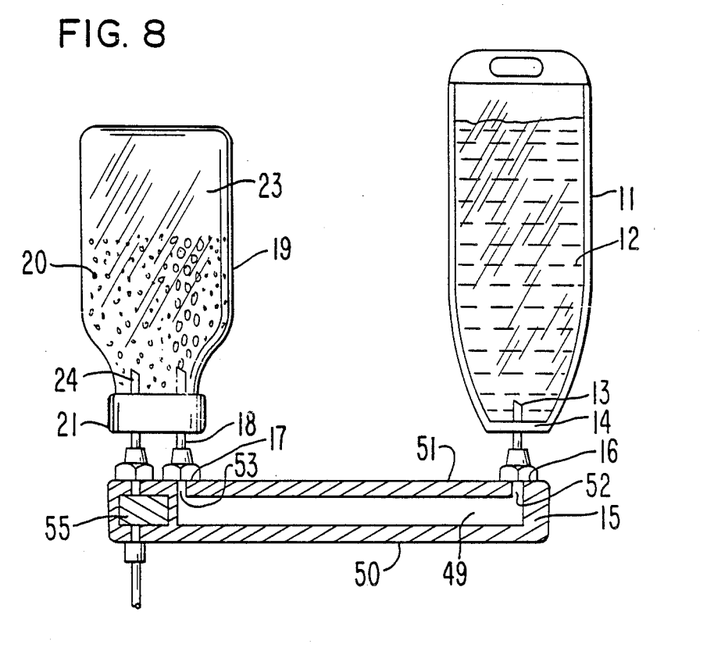
FIG. 8 illustrates an opened view of a manifold having a rate-controlling element suitably mounted in the manifold; and, FIG. 9 illustrates an opened view through the closure area of the vial.
Figure 9:
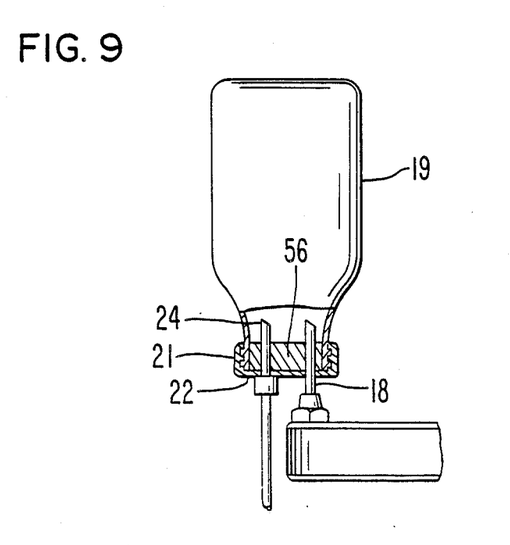

FIG. 6 is a partial view of delivery system 10 as illustrated in FIGS. 1 to 5. In FIG. 6, manifold 15 is seen in opened-section. Manifold 15 comprises a central bore 49 that is an internal conduit or bore for conveying fluid 12 from container 11 to vial 19. Manifold 15 is equipped optionally with a valve 55 for regulating the fluid flow through conduit 49. Manifold 15 is manufactured in one embodiment by first molding base 51 from a plastic or from a metal, and then inserting cover 50 snugly and firmly into base 51. In another embodiment, manifold 15 can be made from a solid piece of material. In this manufacture, manifold 15 is made by drilling a passageway 49 from one side almost through the solid material just until the distant end is reached without penetrating the end, thereby keeping this side closed to the environment. Then, a pair of vertical, laterally positioned passageways 52 and 53 are drilled for connecting the exterior of the manifold with transverse passageway 49. The lateral passageways 52 and 53 are a means for receiving incoming and outgoing spikes. In manifold embodiments wherein the manifold receives and supports both the primary path and the secondary paths, the manifold is made in a like manner. The opening formed on the one-side necessitated by drilling the transverse passageway is conveniently plugged to yield the operative manifold. FIG. 7 is another embodiment of manifold 15 similar to manifold 15 of FIG. 6 with the added feature of an in-line filter 54 in manifold 15. Filter 54 is provided for preventing unwanted materials in fluid 12 from entering vial 19. Also filter 54 can be used in cooperation with flow regulators to regulate fluid flow from reservoir 12 through manifold 15. FIG. 8 is another embodiment of manifold 15 seen in opened section. In FIG. 8, manifold 8 is provided with a membrane 55 formed optionally of a porous or a microporous material. Membrane 55 is provided as a useful aid for further regulating the rate of flow of medical solution 30 being administered to a patient. FIG. 9 depicts vial 19 in opened section at its mouth 22. A stopper 56 is snugly positioned in mouth 22 for closing vial 19. Stopper 56 is made of rubber or plastic easily penetrated by spikes 24 and 18 in a self-sealing engagement.

The novel and unobvious invention uses means for obtaining the precise control of agent delivery in a parenteral delivery system. While there has been described and pointed out features of the invention as applied to presently preferred embodiments, those skilled in the art will appreciate that various modifications, changes, additions, and omissions in the delivery system illustrated and disclosed can be made without departing from the spirit of the invention.

I claim:

1. A method for the administration of a beneficial agent to a warm-blooded animal which method comprises:
   (a) admitting into the animal an agent delivery member in fluid communication with the parenteral delivery system, the delivery system comprising:
      (1) a reservoir of a pharmaceutically acceptable medical fluid;
      (2) a vial containing a pharmaceutically acceptable beneficial solid agent selected from the group consisting of dry, spray-dried and lyophilized beneficial agents that dissolve in the presence of an incoming medical fluid;
      (3) a rigid manifold that provides fluid communication between the reservoir and the vial and which is capable of supporting at least one of the reservoir and the vial and comprises an internal conduit for conveying fluid therethrough;
   (b) permitting fluid to flow from the reservoir through the manifold into the vial to form in the vial a medical solution containing beneficial agent; and,
   (c) administering the agent to the animal by letting the medical solution comprising the beneficial agent flow from the vial to the delivery member, thereby administering the agent to the animal.

2. A parenteral system for administering a beneficial agent to a recipient, the delivery system comprising:
   (a) a reservoir of a pharmaceutically acceptable medical fluid;
   (b) a vial containing a pharmaceutically acceptable beneficial solid agent, said agent a member selected from the group consisting of crystalline, particle, granule, powder, tablet and friable pharmaceutically acceptable forms that formulates a parenterally administrable solution with medical fluid that enters the vial; and,
   (c) a rigid manifold comprising (1) means for establishing fluid communication between the manifold and the reservoir; (2) means for establishing fluid communication between the manifold and the vial; and, (3) means for establishing fluid communication between the reservoir and the vial, and which manifold is capable of supporting the vial when the parenteral system is in operation administering the beneficial agent to a recipient.

3. The parenteral delivery system for administering the beneficial agent to a recipient according to claim 2, wherein the manifold comprises a filter.

4. The parenteral delivery system for administering the beneficial agent to a recipient according to claim 2, wherein the manifold comprises a valve for regulating the flow of fluid from the reservoir to the vial.

5. The parenteral delivery system for administering the beneficial agent to a recipient according to claim 2, wherein the agent is an intravenously administrable drug.

6. A method for the administration of a beneficial agent to a warm-blooded animal, which method comprises:
   (a) admitting into the animal an agent delivery member in fluid communication with a primary path of the delivery system, the delivery system comprising:
      (1) a reservoir of a pharmaceutically acceptable medical fluid;
      (2) a vial comprising from 10 nanograms to 425 grams of a pharmaceutically acceptable beneficial solid agent selected from the group consisting of microcrystalline, pellet, compressed powder, comprises granule and pharmaceutically acceptable forms that disintegrate in the presence of medical fluid that enters the vial and form an agent formulation solution with said medical fluid;
      (3) a primary fluid path; and,
      (4) a supportive manifold that provides internal fluid communication between the reservoir and the vial, and between the vial and the primary fluid path;

(b) permitting fluid to flow from the reservoir through the manifold into the vial to form in situ a medical solution containing beneficial agent; and, (c) administering the agent to the animal be letting the medical solution flow from the vial through the primary path to the delivery member, thereby administering the agent to the animal.

7. A parenteral delivery system for administering a beneficial drug to a recipient, the delivery system comprising:

(a) a reservoir of a pharmaceutically acceptable fluid;

(b) a vial comprising a pharmaceutically acceptable beneficial solid drug;

(c) a primary fluid path; and, (d) a manifold comprising (1) means for establishing fluid communication between the reservoir and the manifold; (2) means for establishing fluid communication between the vial and the manifold; (3) means for establishing fluid communication between the reservoir and the vial, and (4) means for establishing fluid communication between the vial, the manifold and the primary path, and which manifold is capable of supporting at least on of the reservoir and the vial when the parenteral delivery system is in operation formulating a parenterally administrable drug solution and administering the drug solution to a recipient.

8. The parenteral delivery system for administering the beneficial agent to a recipient according to claim 7, wherein the manifold comprises a valve for regulating the flow of fluid from the reservoir to the vial.

9. A method for the administration of a beneficial agent to a warm-blooded animal, which method comprises:

(a) admitting into the animal an agent delivery member in fluid communication with a common path f the delivery system, the delivery system comprising:

(1) a reservoir of a pharmaceutically acceptable medical fluid;

(2) a vial containing a pharmaceutically acceptable beneficial solid agent;

(3) a primary fluid path;

(4) a secondary fluid path;

(5) a rigid manifold that provides fluid communication between the reservoir and the vial, between the vial and the primary path and between the reservoir and the secondary path and is capable of supporting at least one of the reservoir and the vial during operation of the delivery system;

(6) a common path in the fluid communication with the primary path and the secondary path;

(b) permitting fluid to flow through the manifold from the reservoir into the vial to form in situ a medical solution containing beneficial agent;

(c) administering the agent by letting medical solution flow from the vial into the primary path and into the common path to the delivery member, thereby administering the beneficial agent to the recipient.

10. A parenteral delivery system for administering a beneficial agent to a recipient, the delivery system comprising:

(a) a reservoir of a pharmaceutically acceptable fluid;

(b) a vial containing a pharmaceutically acceptable beneficial solid agent;

(c) a primary fluid path;

(d) a secondary fluid path; and, (e) a rigid manifold comprising (1) means for establishing fluid communication between the reservoir and the manifold; (2) means for establishing fluid communication between the vial and the manifold; (3) means for establishing fluid communication between the reservoir and the vial; (4) means for establishing fluid communication between the vial, the manifold, and the primary path; and (5) means for establishing fluid communication between the reservoir, the manifold and the secondary path and which manifold is capable of supporting the reservoir and the vial during operation of the parenteral delivery system.

11. The parenteral delivery system for administering a beneficial agent to a recipient according to claim 10, wherein the manifold comprises a filter.

12. The parenteral delivery system for administering the beneficial agent to a recipient according to claim 10, wherein the manifold comprises a valve for regulating the flow of fluid from the reservoir to the vial.

13. The parenteral delivery system for administering the beneficial agent to a recipient according to claim 10, wherein the agent is an intravenously administrable drug.

14. A parenteral delivery system for administering a beneficial agent to a recipient, the delivery system comprising:

(a) a reservoir of a pharmaceutically acceptable fluid;

(b) a vial containing a pharmaceutically acceptable beneficial solid agent;

(c) a primary fluid path;

(d) a secondary fluid path;

(e) a rigid manifold comprising (1) means for establishing fluid communication between the reservoir and the manifold; (2) means for establishing fluid communication between the vial and the manifold; (3) means for establishing fluid communication between the reservoir and the vial; (4) means for establishing fluid communication between the vial, the manifold, and the primary path; and (5) means for establishing fluid communication between the reservoir, the manifold and the secondary path and which is capable of supporting at least one of the reservoir and the vial; and, (f) a common path in fluid communication with the primary path and in fluid communication with the secondary path.

15. A parenteral delivery system for forming a beneficial agent solution for administering to a recipient, wherein the delivery system comprises:

(a) a reservoir comprising a pharmaceutically acceptable fluid;

(b) a vial comprising a pharmaceutically acceptable agent;

(c) a rigid manifold for establishing fluid communication between the reservoir and the vial and which is capable of supporting at least one said reservoir and said vial, wherein the manifold comprises:

(1) an internal conduit for conveying fluid therethrough;

(2) means for connecting the reservoir to the manifold;

(3) means for connecting the vial to the manifold; and, (4) a valve for regulating fluid flow through the conduit; and wherein when the delivery system is in operation the pharmaceutically acceptable fluid flows through the conduit into the vial for forming a parenterally administrable agent solution with the pharmaceutically acceptable agent.

16. A parenteral delivery system for administering a beneficial agent to a recipient, the delivery system comprising:
   (a) a reservoir of a pharmaceutically acceptable medical fluid;
   (b) a vial containing a pharmaceutically acceptable beneficial solid agent that dissolves in the presence of incoming medical fluid and forms a medical solution comprising the beneficial agent; and,
   (c) a rigid manifold comprising (1) means for establishing fluid communication between the manifold and the reservoir; (2) means for establishing fluid communication between the manifold and the vial; (3) means for establishing fluid communication between the reservoir and the vial; (4) a valve for regulating fluidn flow; and which manifold is capable of supporting the reservoir and the vial when the parenteral system is in operation administering the beneficial agent to a recipient.

* * * * *